US006677584B2

(12) United States Patent
Yonushonis

(10) Patent No.: US 6,677,584 B2
(45) Date of Patent: Jan. 13, 2004

(54) MANUFACTURING FLUID INCLUDING FLUORESCENT DYE PENETRANT AND METHOD FOR USING TO MAKE COMPONENTS

(75) Inventor: Tom Yonushonis, Columbus, IN (US)

(73) Assignee: Cummins Inc., Columbus, IN (US)

( * ) Notice: Subject to any disclaimer, the term of this patent is extended or adjusted under 35 U.S.C. 154(b) by 59 days.

(21) Appl. No.: 09/886,996

(22) Filed: Jun. 25, 2001

(65) Prior Publication Data

US 2002/0195560 A1 Dec. 26, 2002

(51) Int. Cl.⁷ .......................... G01T 1/161; C09K 11/06
(52) U.S. Cl. ................... 250/302; 252/309.19
(58) Field of Search ................ 250/302, 301, 250/461.1; 252/301.19, 301.16, 960, 408.1

(56) References Cited

U.S. PATENT DOCUMENTS

| | | |
|---|---|---|
| 3,184,596 A | 5/1965 | Alburger |
| 3,652,224 A | 3/1972 | Johnson et al. ............ 23/230 R |
| 3,716,492 A * | 2/1973 | Graham et al. ......... 252/301.19 |
| 3,777,143 A | 12/1973 | Winans et al. ............... 250/302 |
| 3,896,664 A * | 7/1975 | Alburger ....................... 73/104 |
| RE28,605 E | 11/1975 | Alburger ....................... 106/19 |
| 3,981,185 A | 9/1976 | Molina ......................... 250/302 |
| 4,172,224 A | 10/1979 | Lapinski et al. ............. 250/302 |
| 4,331,871 A | 5/1982 | Allinikov ..................... 250/302 |
| 4,400,618 A | 8/1983 | Bupp et al. .................. 250/302 |
| 4,621,193 A | 11/1986 | Van Hoye .................... 250/302 |
| 5,115,136 A | 5/1992 | Tomasch .................. 250/461.1 |
| 5,667,840 A * | 9/1997 | Tingey et al. ................... 427/8 |
| 6,070,455 A * | 6/2000 | Cavestri ....................... 73/40.7 |

* cited by examiner

Primary Examiner—John R. Lee
Assistant Examiner—James J. Leybourne
(74) Attorney, Agent, or Firm—Nixon Peabody LLP; Tim L. Brackett, Jr.

(57) ABSTRACT

A reliable and cost-effective method and composition is provided for inspecting manufactured components and detecting defects therein. In particularly, a method is provided for optically detecting defects in manufactured components during the manufacturing process by the incorporation of a fluorescent dye into a manufacturing fluid.

24 Claims, 2 Drawing Sheets

(2 of 2 Drawing Sheet(s) Filed in Color)

MANUFACTURING FLUID INCLUDING FLUORESCENT DYE PENETRANT AND METHOD FOR USING TO MAKE COMPONENTS

FIELD OF THE INVENTION

This invention relates to a manufacturing fluid containing a fluorescent dye and method of use for detecting defects in components undergoing machining operations and further relates to ceramic components formed by the manufacturing process.

BACKGROUND OF THE INVENTION

The use of a coatable material to detect defects in the surface of an object is well known as illustrated for example in U.S. Pat. No. 3,777,143 to Winans et al. which discloses an aqueous solution that can be coated onto the surface, dried and partially removed except for a coating retained by surface openings and flaws. Such coatings and methods of using the coating are known generally as "liquid penetrant inspection." Among the many advantages of these techniques are their non-destructive nature and their ability to allow optical detection of minute surface defects that could not otherwise be optically detected.

Development of liquid penetrant inspection systems and techniques have focused on a variety of different approaches. For example, in U.S. Pat. No. 3,652,224 to Johnson et al. a method is disclosed for enlarging the cracks via a process of corrosion in order to allow the cracks to be detected by conventional penetrating dye liquid. In U.S. Pat. No. 3,981,185 to Molina a system and method is disclosed for applying a dye penetrant, such as a fluorescent dye, that may be applied in a more or less conventional manner followed by the application or a emulsifier to treat the penetrant covered surface to remove the excess penetrant without removing dye penetrant from the cracks and flaws. While this process simplifies the steps involved in removing the excess penetrant, considerable time and expense can still be involved in performing the type of process steps disclosed in this patent.

Still further innovation in liquid penetrant inspection systems has occurred in the composition of the penetrant. For example, U.S. Pat. No. RE 28,605 to Alburger discloses a penetrant containing a solvent ingredient which acts to provide a low degree of emulsifiability to provide improved reliability of flaw indications. U.S. Pat. No. 4,172,224 to Lapinski discloses the concept of using silver nitrate solution to allow detection of microcracks. None of these improved compositions or processes has fully addressed the need for simplifying the steps and costs of employing the resulting liquid penetrant inspection process to make it generally attractive and cost effective.

Development of a variety of different applications or unique delivery systems or techniques have allowed the liquid penetrant inspection concept to be applied to specific environments or problems. For example, U.S. Pat. No. 4,621,193 to Van Hoye discloses a crack detection system including a novel applicator for delivering a fluorescent dye penetrant to provide a more effective system for detecting minute surface flaws. The patent to Tomasch (U.S. Pat. No. 5,115,136) discloses an inspection system which enables the operator to detect minute cracks and flaws in normally inaccessible places of manufactured parts. Still these approaches do not solve the problem of making liquid penetrant inspection cost effective across a broad range of applications.

Liquid penetrant inspection has the potential for broad application as demonstrated in U.S. Pat. No. 4,400,618 to Bupp et al. which discloses a fluorescing dye method for detecting flaws in printed circuit boards. The patent to Alburger (U.S. Pat. No. 3,184,596) is notable for its disclosure of a liquid penetrate inspection system including a detection method that uses fluorescent color dye penetrant to detect minute porosities or fracture cracks in ceramic parts using an ultraviolet light (see col. 1, lines 8–14 and col. 2, lines 70–71). U.S. Pat. No. 4,331,871 to Allinikov discloses a method for detecting flaws in the surface of a workpiece such as engine parts where a fluorescent dye is used to highlight the flaws which may be inspected under an ultraviolet light (see col. 2, lines 47–62).

Ceramic materials have a number of properties that make them extremely useful in applications demanding close tolerances, long operating life and insensitivity to high temperature environments. One particularly important commercial application has been as a component in a high pressure fuel system for diesel engines as disclosed in commonly assigned U.S. Pat. No. 5,899,383. This application requires a material that is capable of operating under very demanding conditions of high pressure (15,000 to 20,000 psi and above) and high temperature. In addition, diesel fuel systems demand components that can operate over extensive periods while in contact with diesel fuel which has low lubricity properties and which may include abrasive particles that cause high failure rates when metal plungers are used.

As disclosed in U.S. Pat. No. 5,899,383, plungers made of certain types of ceramic material have been shown to have unexpectedly favorable operating characteristics in high pressure fuel systems. However, to achieve these operating characteristics the ceramic plunger must be formed to very exacting dimensions and must be essentially defect free. To form ceramic plungers having these characteristics requires the plungers to be subjected to grinding operations. Typically, conventional water-based grinding coolant or cutting fluids are used to allow the grinding operation to achieve the required shape and dimensions.

Acceptable plungers must have sharp edges. This gives rise to a tendency in a relatively small percentage of plungers (e.g. 1 in a 1000) to the formation of chips and closed cracks that are difficult to detect optically. Fluorescent dye penetrant can be used to highlight these defects but use of this technique requires the ceramic plunger to be subjected to a number of additional handling steps that increase the cost of manufacture.

While the compositions, processes and applications disclosed in the prior art may be suitable to achieve their disclosed purposes, no disclosure has been made of a system that is entirely satisfactory in achieving the broad objectives of effectiveness, low cost and efficiency.

SUMMARY OF THE INVENTION

It is a primary object of this invention to overcome the deficiencies of the prior art by providing a fluorescent penetrant system that is substantially more effective, low in cost and more efficient than are the systems disclosed in the prior art.

Another object of the subject invention is to provide a method for forming a component using a manufacturing fluid which facilitates formation and inspection of the component including the steps of adding a fluorescent dye to the manufacturing fluid, subjecting the component to a forming step using the manufacturing fluid including the fluorescent dye, and inspecting the component for surface cracks or defects following the forming step.

Yet another object of the subject invention is to provide a method as described above wherein the forming step includes the step of cutting the component material while applying the manufacturing fluid containing the fluorescent dye.

Still another object is to provide a method for grinding a ceramic material while applying the manufacturing fluid containing the fluorescent dye.

Another object of the invention is to provide a method as described above wherein the manufacturing fluid is an aqueous coolant/lubricant and wherein the fluorescent dye is present in the manufacturing fluid in a dilution range of 1 to 5 parts per 10,000 parts of water.

Another object of the invention is to provide a method as described above wherein the step of providing fluorescent dye includes the step of adding the fluorescent dye to a concentration of between 125 to 500 parts per million.

Still another object of the invention is to provide a method as described above wherein the step of providing fluorescent dye includes the step of adding the fluorescent dye to a concentration of approximately 250 parts per million.

Yet another object is to provide a method as described above wherein the fluorescent dye is DUBL-CHECK A-416 FLUORESCENT TRACER® or any other commercially available concentrated additive suitable for hydrostatic leak testing.

Another object is to provide a method as described above for manufacturing a ceramic component wherein the manufacturing step includes the step of grinding the ceramic component to a desired shape and the inspection step includes the step of optically inspecting the surface of the ceramic component.

Yet another object is to provide a method as described above wherein the grinding step includes grinding sharp edges which are subject to chips and closed cracks but which can be optically detected when contacted by the fluorescent dye penetrant during the grinding step.

Still another object is to provide a method as described above wherein the forming process forms a ceramic plunger for a fuel system that is ground to within 1.93 to 3.25 microns tolerance.

It is another object to provide a manufacturing fluid for facilitating formation and inspection of a component including a manufacturing fluid suitable for facilitating the formation of the component, and a fluorescent dye at a concentration sufficient to highlight surface defects and cracks upon completion of the formation step.

Another object is to provide a manufacturing fluid as defined above wherein the manufacturing fluid is a grinding fluid and/or a cutting fluid.

Still another object is to provide a manufacturing fluid as defined above wherein the manufacturing fluid is an aqueous coolant/lubricant and wherein the step of providing fluorescent dye includes the step of adding fluorescent dye in a dilution range of 1 to 5 parts per 10,000 parts of water and particularly 250 ppm of water in the manufacturing fluid and still more particularly wherein the fluorescent dye is DUBL-CHECK A-416 FLUORESCENT TRACER®.

Yet another object is to provide a method for making a ceramic component conforming closely to predetermined dimensions within acceptable tolerances, including the steps of forming a ceramic element having dimensions that exceed the predetermined dimensions, removing excess ceramic material to cause the ceramic element to conform to the predetermined dimensions within the acceptable tolerances, forming a manufacturing fluid including the step of adding a fluorescent dye to the manufacturing fluid to a level of dilution that cause surface defects and closed cracks to be optically detectable, and applying the manufacturing fluid with fluorescent dye during the removal step.

Still another object is to provide a ceramic component as described above wherein the ceramic forming step includes the step of forming a ceramic component that is suitable for use in a high pressure fuel system such as for example a ceramic plunger having sharp edges which are susceptible to chips and closed cracks which normally can not be easily detected. By addition of fluorescent dye in the manufacturing fluid such chips and closed cracks can be much more easily detected optically.

Still other and more specific objects of the subject invention can be ascertained by considering the following Brief Description of the Drawings and Detailed Description.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION

Figure 1:
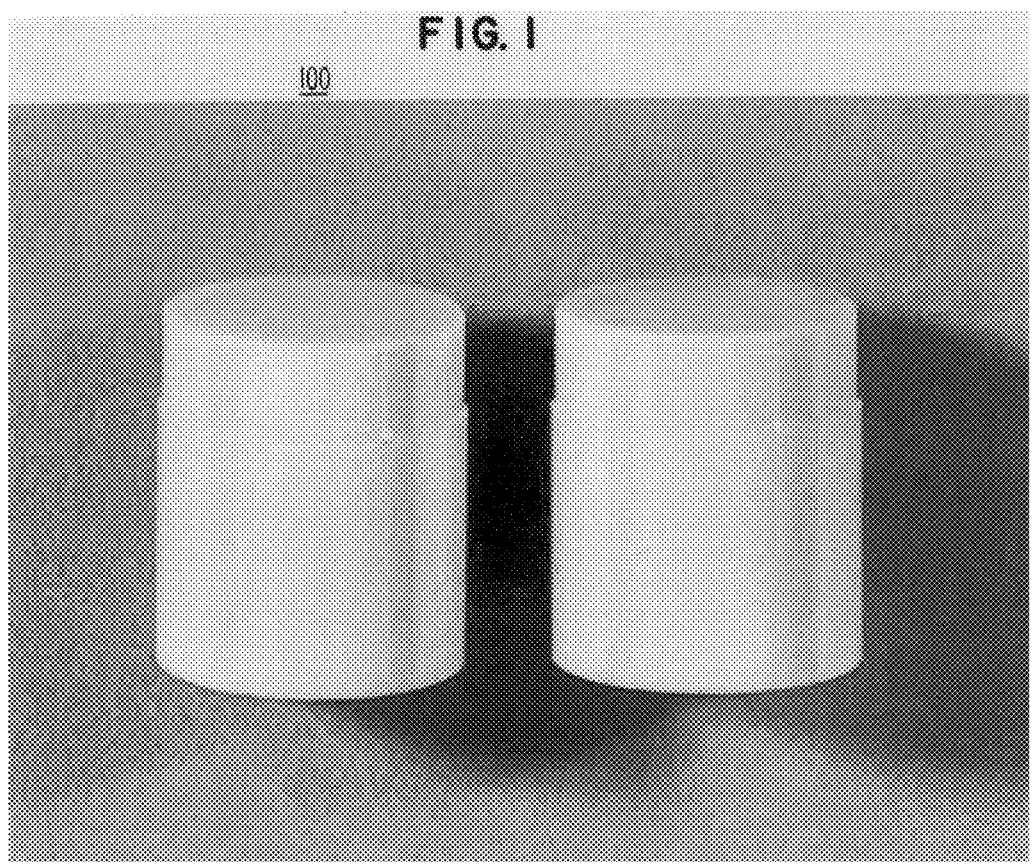
FIG. 1 is a photomicrograph of a ceramic plunger subjected to a grinding process using a conventional grinding fluid.

The subject invention relates to the formation of components, such as ceramic components, that need to be relatively free of chips, cracks and other types of surface defects. The need for this type of ceramic component is particularly acute in fuel systems such as fuel systems for compression ignition internal combustion engines. In this environment, components are often required to operate under widely varying temperatures and at extremely high pressures. For moving components that come into contact with fuel, such as diesel fuel, the operating environment is even more extreme because fuel, such as diesel fuel, has relatively poor lubricating properties and moving parts are required to fit with extremely close tolerances to insure adequate sealing characteristics in high pressure fuel systems. Certain types of ceramic materials have been found to work well in forming critical components of fuel systems such as plunger elements mounted for reciprocal movement within bores formed in metal housings. For example, ceramic plungers have proven to be particularly useful as the timing plunger, such as disclosed in commonly assigned U.S. Pat. No. 5,899,383, and as the rotor of a fuel distributor, as disclosed in commonly assigned U.S. Pat. No. 5,713,333. The disclosure of these patents is hereby incorporated by reference.

For ceramic components to satisfy rigorous operating requirements such as described above, it is often important that the ceramic components be manufactured in very precise dimensions. For example, timing plungers formed in accordance with the invention described in U.S. Pat. No. 5,899,383 needs to form a clearance with surrounding wall of the bore within which it is placed of between 76 to 128 millionths of an inch (1.93 to 3.25 microns). To achieve such precise tolerances typically requires that the ceramic component initially be formed with oversized dimensions so that the excess can be removed during a manufacturing step such as by cutting or grinding which can give rise to chips, cracks and other types of surface defects that are difficult to observe by optical inspection. This phenomenon is particular troublesome when the component is formed with sharp edges such as required in forming suitable fuel injector plungers.

To highlight the surface defects of ceramic, it is known to use a fluorescent dye penetrant such as disclosed in U.S. Pat. No. 3,184,596 to Alburger and U.S. Pat. No. 4,331,871 to Allinikov. This approach is particularly effective where the grinding process leaves broken atomic bonds which are active. However, applying such penetrant subsequent to the grinding operation adds additional steps and costs to the manufacture of acceptable ceramic components.

According to the subject invention, fluorescent dye is added to the manufacturing fluid used in the grinding process for removing excess ceramic material. The grinding process continues until the oversized ceramic component achieves the desired dimensions, within acceptable tolerances. The amount of fluorescent dye added should be limited to avoid interference with the ordinary function of the manufacturing fluid. At the same time a sufficient amount of fluorescent dye is added to cause surface defects to be optically detectable. For example, for an aqueous grinding fluid such as CIMTECH 500®, a fluorescent dye can be added to a dilution of 1 to 5 parts per 10,000 parts of water. DUBL-CHECK A-416 FLUORESCENT TRACER® manufactured by Sherwin Incorporated has been found to be particularly suitable at 250 ppm. Concentrations as low as 125 ppm concentration has been shown to be only slightly less bright. Concentrations as high as 500 ppm or higher may be used in certain circumstances.

While grinding fluid as described above has been shown to be highly effective, any water-based manufacturing fluids could be employed. The type of fluorescent dye used can also be varied depending on the circumstances. In general, any commercially available concentrated additives for hydrostatic leak testing could be employed. For example, the following are tradenames for various fluorescent dyes that may be employed in the present invention: TRACERLINE TP-3900®, TRACERLINE TP 3390®, TRACERLINE TP 3920®. UVP REVEAL A-690PLUS®, and American Gas and Chemical Co., Ltd. FA-1A® water additive. Additional manufacturers of fluorescent dyes which can be employed include, for example, SPECTROLINE®, FLUORO-DYE®, AND MAGELlAN DIAGNOSTICS®.

FIG. 1 is a photomicrograph of a ceramic plunger 100 that has been ground to suitable dimension suitable for use within a unit fuel injector of the type disclosed in U.S. Pat. No. 5,899,383. This plunger was subjected to a grinding process in the absence of fluorescent dye. The grinding fluid employed was a 5% solution of CIMTECH 500®manufactured by Milacron, Inc. No surface defects are readily apparent under ultra-violet light.

Figure 2:
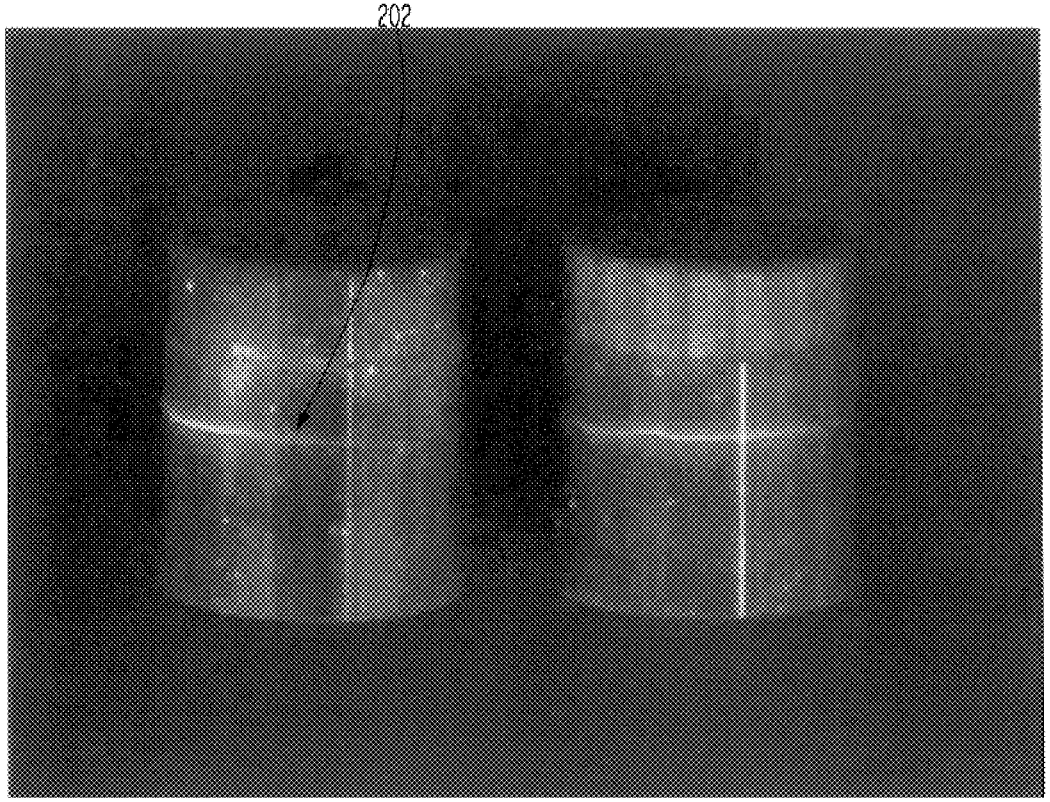
FIG. 2 is a photomicrograph of a ceramic plunger subjected to a grinding process using a grinding fluid containing a fluorescent dye.

FIG. 2 is a photograph/micrograph of a ceramic plunger 200 subjected to a grinding process using CIMTECH 500®grinding fluid with DUBL-CHECK A-416 FLUORESCENT TRACER® added at a concentration of 250 ppm. In this photograph, surface defects 202 are readily apparent under ultra-violet light. Such defects would be much harder to detect without the use of fluorescent dye in the grinding fluid yet no addition manufacturing or handling steps are required.

What is claimed is:
1. A method for forming a component using a manufacturing fluid which facilitates formation and inspection of the component, comprising the steps of
 a. adding a fluorescent dye to the manufacturing fluid,
 b. subjecting the component to a forming step selected from grinding or cutting while applying the manufacturing fluid including the fluorescent dye, and
 c. inspecting the component for surface cracks or defects following the forming step.
2. The method of claim 1, wherein the manufacturing fluid is an aqueous coolant/lubricant and wherein step a. of providing fluorescent dye includes the step of adding fluorescent dye in a dilution range of 1 to 5 parts per 10,000 parts of water.
3. The method of claim 1, wherein step a. of providing I. fluorescent dye includes the step of adding fluorescent dye to a concentration of between 125 to 500 parts per million.
4. The method of claim 1, wherein step a. of providing fluorescent dye includes the step of adding fluorescent dye to a concentration of approximately 250 parts per million.
5. The method of claim 1 wherein in step a. said fluorescent dye is DUBL-CHECK A-416 FLUORESCENT TRACER®.
6. The method of claim 1, wherein the component is a ceramic component and, wherein step b. includes the step of grinding the ceramic component to a desired shape and step c. includes the step of optically inspecting the surface of the ceramic component.
7. The method of claim 1, wherein the component is a ceramic component and, wherein step c. includes the step of inspecting the component for surface cracks or defects under ultra-violet light.
8. The method of claim 6, wherein the step of grinding the ceramic component includes the step of grinding sharp edges which are subject to chips and closed cracks.
9. The method of claim 8, wherein the forming process forms a ceramic plunger for a fuel system that is ground to within 1.93 to 3.25 microns tolerance.
10. A manufacturing fluid for facilitating formation and inspection of a component, comprising
 a grinding fluid,
 a fluorescent dye at a concentration sufficient to highlight surface defects and
 cracks upon completion of the formation step.
11. A manufacturing fluid as defined in claim 10, wherein the manufacturing fluid is a coolant.
12. A manufacturing fluid as defined in claim 10, wherein the manufacturing fluid is a lubricant.
13. A manufacturing fluid as defined in claim 10, wherein the grinding fluid is CIMTECH 500®.
14. A manufacturing fluid as defined in claim 10, wherein the manufacturing fluid is a cutting fluid.
15. A manufacturing fluid as defined in claim 10, wherein the concentration of fluorescent dye is approximately 250 ppm of water in the manufacturing fluid.
16. A manufacturing fluid as defined in claim 10, wherein the fluorescent dye is DUBL-CHECK A-416 FLUORESCENT TRACER®.
17. A method for making a ceramic component having predetermined dimensions within acceptable tolerances, comprising the steps of
 a. forming a ceramic element having dimensions that exceed the predetermined dimensions,
 b. removing excess ceramic material to cause the ceramic element to conform to the predetermined dimensions within the acceptable tolerances, c. forming a manufacturing fluid for assisting step b. including the step of adding a fluorescent dye to the manufacturing fluid to a level of dilution that causes surface defects and closed cracks to be optically detectable, and d. applying the manufacturing fluid with fluorescent dye formed in step c. during the removal step b.

18. The method as defined in claim 17 wherein step b. includes the step of forming a ceramic component that is suitable for use in a high pressure fuel system.

19. The method as defined in claim 17 wherein step b. further includes the step of forming a ceramic plunger having sharp edges which are susceptible to chips and closed cracks which normally can not be easily detected optically but for the addition of fluorescent dye in the manufacturing fluid.

20. The method as defined in claim 17 wherein step b. includes the step of grinding the ceramic and step c. further includes the step of forming a manufacturing fluid which is a grinding fluid.

21. The method as defined in claim 17 wherein step c. includes forming the manufacturing fluid as an aqueous fluid and adding the fluorescent dye to a level of 1 to 5 parts per million of water.

22. The method of claim 17 wherein step c. includes forming the manufacturing fluid as an aqueous fluid and adding the fluorescent dye to a concentration between 125 to 500 parts per million.

23. The method of claim 17 wherein step c. includes forming the manufacturing fluid as an aqueous fluid and adding the fluorescent dye to a concentration of approximately 250 parts per million.

24. The method as defined in claim 21 wherein the fluorescent dye is DUBL-CHECK A-416 FLUORESCENT TRACER®.

* * * * *